United States Patent [19]

Cottenden

[11] Patent Number: 5,702,381
[45] Date of Patent: Dec. 30, 1997

[54] MALE INCONTINENCE DEVICE

[75] Inventor: Alan M. Cottenden, Brickhill, England

[73] Assignee: McNeil-PPC, Inc., Skillman, N.J.

[21] Appl. No.: 751,037

[22] Filed: Nov. 15, 1996

Related U.S. Application Data

[63] Continuation of Ser. No. 315,380, Sep. 30, 1994, abandoned.

[30] Foreign Application Priority Data

Aug. 19, 1994 [GB] United Kingdom .................. 9416876

[51] Int. Cl.$^6$ .................................................. A61F 13/15
[52] U.S. Cl. .................. 604/385.1; 604/358; 604/368; 604/349
[58] Field of Search ........................... 604/349, 358, 604/385.1, 385.2

[56] References Cited

U.S. PATENT DOCUMENTS

| | | | |
|---|---|---|---|
| 3,561,446 | 2/1971 | Jones, Sr. ........................... | 604/385.2 |
| 4,655,760 | 4/1987 | Morman et al. ..................... | 604/385.2 |
| 4,808,178 | 2/1989 | Aziz et al. ........................... | 604/385.2 |
| 4,946,454 | 8/1990 | Schmidt .............................. | 604/385.1 |
| 5,275,591 | 1/1994 | Mavinkurve ......................... | 604/387 |

FOREIGN PATENT DOCUMENTS

| | | | |
|---|---|---|---|
| 8109133 | 4/1981 | France ................................. | 604/358 |
| 564904 | 11/1932 | Germany ............................ | 604/385.1 |

*Primary Examiner*—John G. Weiss
*Assistant Examiner*—Dennis Ruhl

[57] ABSTRACT

An absorbent product useful as a male incontinence device is disclosed. The product is convertible between a two-dimensional structure for storage and a three-dimensional structure for use. There are folds forming pleats located in the interior of the product to allow the interior to be expanded from a pleated configuration to an expanded configuration, and the periphery of the product is secured to prevent substantial expansion. Thus, the product is capable of being manipulated between a substantially two-dimensional planar structure for storage and a three-dimensional, cup-like structure for use. Methods of manufacturing these absorbent products are also disclosed.

21 Claims, 7 Drawing Sheets

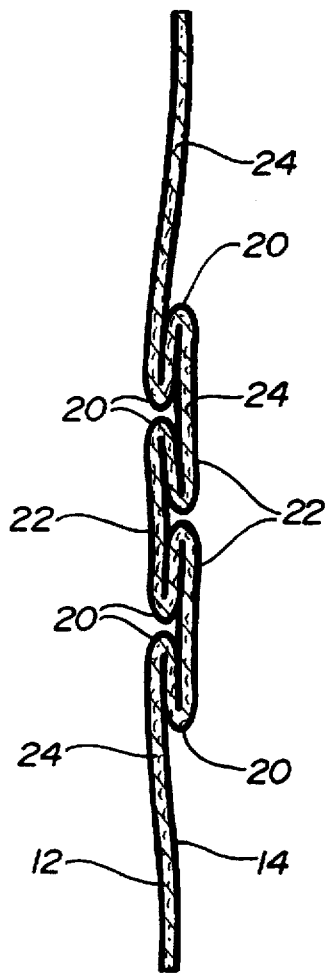
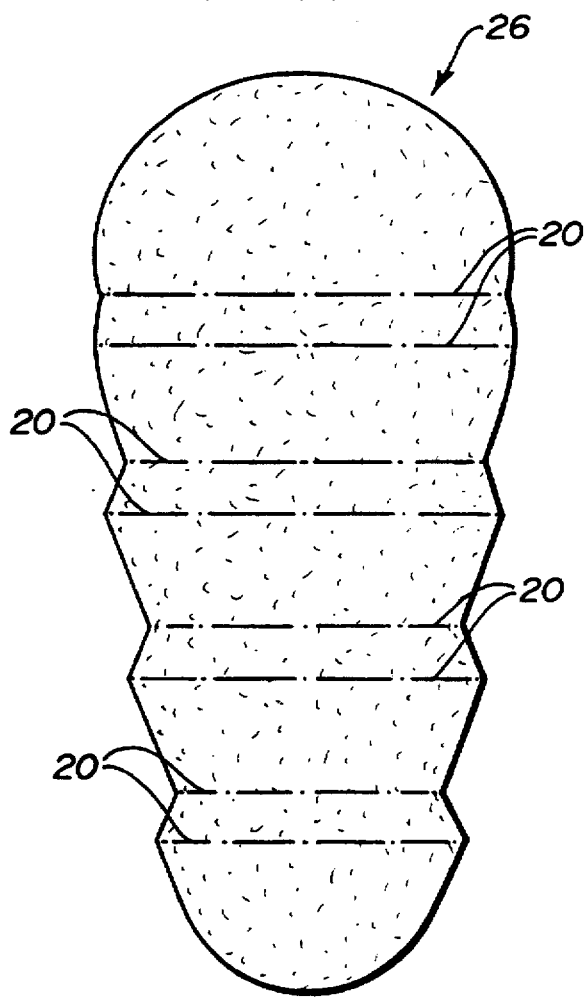
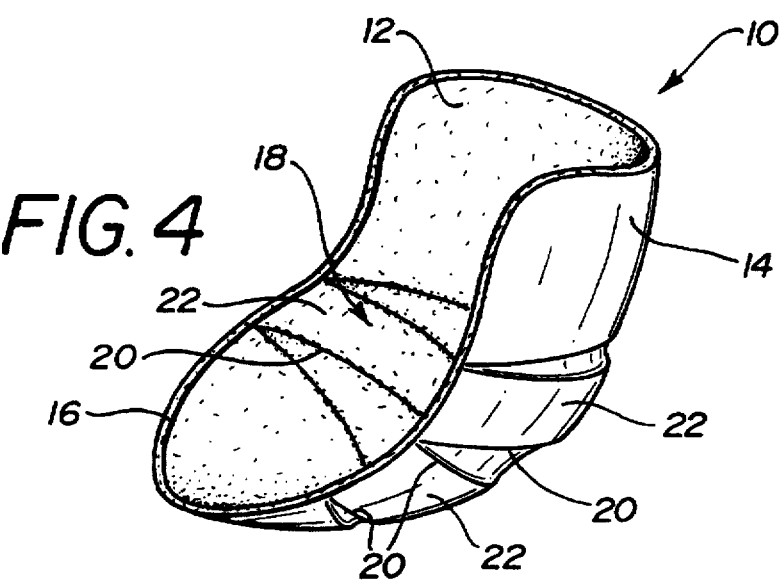

MALE INCONTINENCE DEVICE

This is a continuation of application Ser. No. 08/315,380, filed Sep. 30, 1994, now abandoned.

FIELD OF THE INVENTION

The present invention relates to an absorbent product useful as a male incontinence device which is convertible between a substantially planar structure for storage and a three-dimensional structure for use.

BACKGROUND OF THE INVENTION

It is estimated that some 3% of community-dwelling men under 60 and around 12% of those over 60 suffer from urinary incontinence. A. R. Herzog et al., "Prevalence and Incidence of Urinary Incontinence in Community-Dwelling Populations", *Journal American Geriatric Society*, Vol. 38, pp.273–281 (1990). Of these men, the largest group comprises those whose incontinence is associated with hardening of the prostate (benign prostatic hypertrophy) or associated with the aftermath of surgery for this condition. Such people generally leak quantities of urine which are small, but without protection, are large enough to produce wet patches in their undergarment and often in their outer clothes. Prostate problems most commonly occur in elderly men. However, the first signs of urinary incontinence may appear in men in their fifties, and symptoms generally get worse over time.

Urinary leakage generally occurs under two circumstances. First, it often occurs in the period following micturition. The section of the urethra distal to the prostate fails to empty during micturition, and the urine dribbles out slowly soon after. This phenomenon is known as post micturition dribble. Second, leakage may occur on coughing, sneezing and the like. This is analogous to stress incontinence in women. Either way, sufferers will rarely leak more than 50 ml over a period of several hours.

There are several incontinence products which are described in patent and marketing literature. One category of male incontinence devices is the external catheter type. This type generally comprises a rubber condom which empties into a drainage bag. The drainage bag is usually strapped onto the leg. However, for most active men with small urinary leakage quantities, this type of incontinence device is unnecessarily restrictive and provides excessive protection. It prevents the wearer from emptying his bladder normally, interferes with intimate relations and presents a real risk of skin damage by constantly bathing the skin of the penis in urine. In addition, the drainage bag is bulky beneath clothing and needs to be washed or replaced frequently.

A second category of male incontinence devices is a disposable pouch which is designed to contain at least the end of the penis. Examples of this type of device are disclosed in Larko, U.S. Pat. No. Des. 263,169, which illustrates such a pouch and Smith, U.S. Pat. No. 4,601,716, which discloses a disposable sheath which is closable about the distal end of the penis. These products are difficult to position, tend to migrate with movement and require an unretracted penile shaft.

Recently, modifications of the disposable pouch have been developed which enclose both the penis and scrotum of the wearer. An example of such a device is disclosed in Rooyakkers, U.S. Pat. No. 4,675,012. This patent discloses a deep absorbent pouch for male genitalia having a generally triangular opening wherein one side of the triangle is adapted to be worn flat against the upper genital region and the other two portions of the triangular opening extend into the crotch and meet behind the scrotum. The pouch may be formed by folding and securing portions of a sheet of absorbent material, or it may be formed by molding or deforming a soft foam sheet.

Therefore, what is needed is an easily manufactured, male incontinence device capable of coping reliably with small quantities of urine and imposing minimal restrictions on the normal life of the user. Such a product is preferably very thin, and is convertible between a substantially planar structure for storage and a three-dimensional structure for use.

SUMMARY OF THE INVENTION

I have devised a new male incontinence product which is useful for lightly incontinent men which has a fluid-permeable body-facing surface, a fluid-impermeable garment-facing surface and an absorbent structure between the two surfaces. The product has a periphery and an interior, the periphery is secured to prevent substantial expansion, and the interior has pleats to allow the product to be articulated between a substantially planar structure and a three-dimensional, cup-like structure for use. The product may also include means for securing the product to a user's clothing.

Products such as those described above can be formed by pleating a continuous web of a composite absorbent structure which has an absorbent layer disposed between and in fluid communication with a liquid-impervious barrier layer and a liquid-pervious cover layer. The continuous web preferably has a length dimension substantially greater than a width dimension. The periphery of the absorbent product can be defined in the continuous web and treated where pleated to resist substantial expansion of the pleats at the periphery. The finished absorbent product can then be removed from the continuous web. In an alternative embodiment, the individual cover, barrier and absorbent layers can be pleated before being combined into a composite structure.

BRIEF DESCRIPTION OF THE DRAWING

FIG. 3 is a sectional view along line III—III of FIG. 2.

FIG. 4 is a perspective view of the incontinence product of FIGS. 1–3 in an expanded configuration.

FIG. 5 is a plan view of an absorbent structure prior to pleating useful in the incontinence product of FIGS. 1–3.

DETAILED DESCRIPTION OF THE INVENTION

Figure 2:
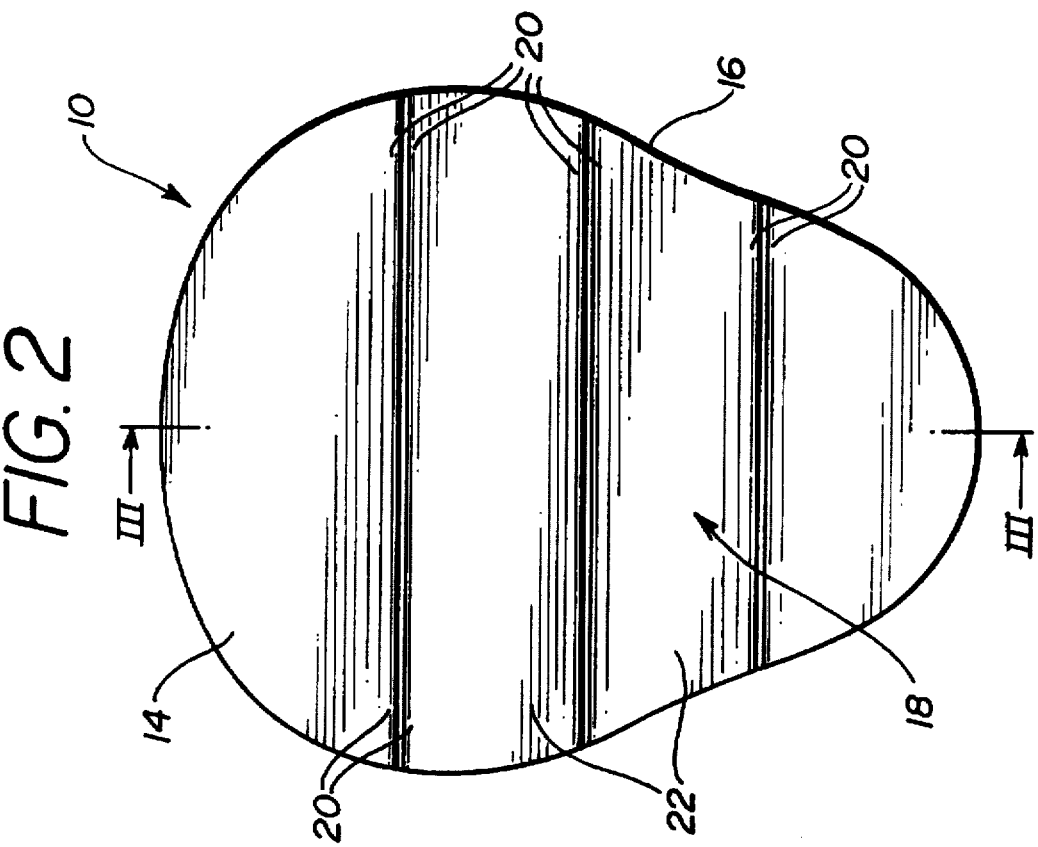
FIG. 2 is a plan view of the garment-facing side of the incontinence product of FIG. 1.
Figure 1:
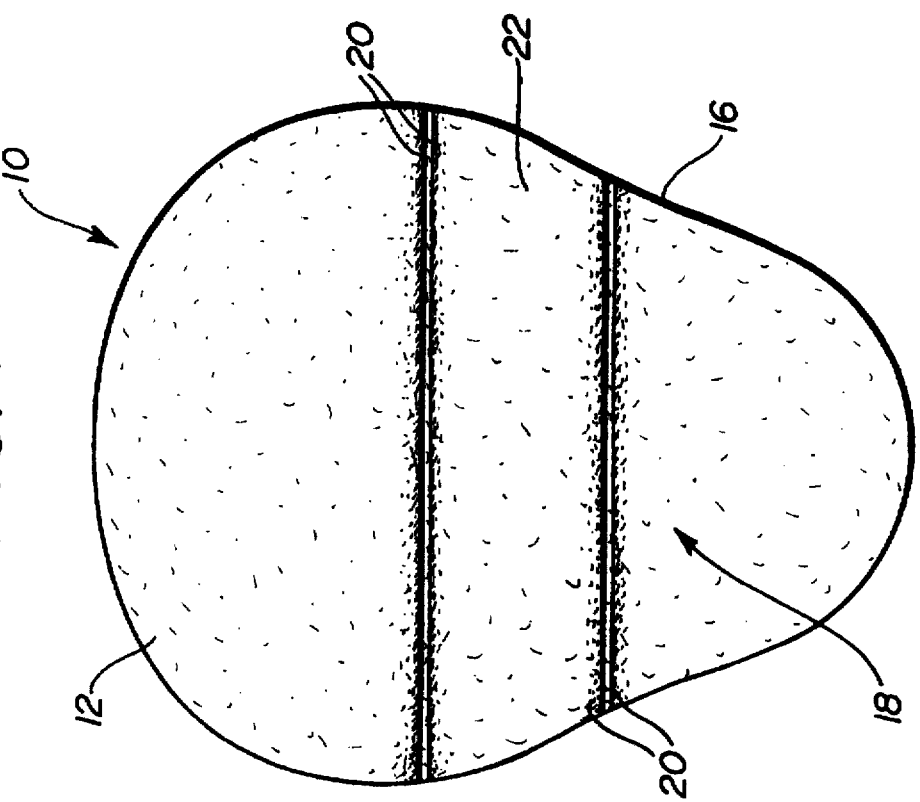
FIG. 1 is a plan view of the body-facing side of an incontinence product in a substantially planar configuration.

Referring to FIGS. 1–4, there is disclosed a male urinary incontinence product 10, having a liquid-permeable, body-facing surface 12 and a liquid-impermeable, barrier layer 14. The product 10 has a periphery 16 and an interior 18. The periphery 16 is secured to prevent significant expansion, while the interior 18 has a plurality folds 20 forming freely-movable pleats 22 to allow the interior 18 to be manipulated into an expanded configuration (FIG. 4). While the pleats 22 may extend to the periphery 16, the folds 20 are secured there to prevent their unfolding and expansion. The periphery 16 may be treated by any means useful to resist expansion of the components of the incontinence product 10. A representative, non-limiting list of useful treating means includes heat sealing, crimping, sewing, adhesive attachment, stapling, and the like. The periphery 16 may also incorporate elastic means 23 to allow for some restricted expansion. Of course, the elastic means restrict substantial expansion of the periphery 16. The periphery 16 may be secured at its outside margin, or it may be secured within approximately 1 cm from the outside margin. Preferably, the periphery 16 is secured within about 5 mm from the outside margin.

The liquid-permeable, body-facing surface 12 may be a separate component such as a cover sheet, or it may be the exposed surface of the absorbent core 24 of the incontinence product 10. Materials useful as cover sheets include, without limitation, knitted, woven, and nonwoven fabrics, apertured films and fabrics, and the like. Cover sheets may be affixed to the exposed surface of the absorbent core 24 (see e.g., FIG. 3), or they may simply cover and enclose the absorbent core 24 (see e.g., FIG. 6). If the cover sheets are affixed to the exposed surface of the absorbent core 24, they may be occasionally or completely attached to that surface. This attachment may be formed by embossing, adhesives, heat sealing and the like. If the cover sheets merely enclose the absorbent core 24, they may be attached to the absorbent core 24 only at the periphery 16, or they may not be attached to the absorbent core 24 at all. For example, the absorbent core 24 may only be affixed to the barrier layer 14.

The liquid-impermeable, barrier layer 14 of the incontinence product 10 may be, without limitation, a plastic film, an impregnated fabric, flexible, polymeric foam shell and the like. The barrier 14 is preferably formed of a flexible material which moves easily between a folded, two-dimensional configuration and an expanded three-dimensional structure.

The absorbent core 24 can be any absorbent structure normally used in sanitary protection, feminine hygiene, infant diaper or adult incontinence products. Preferably, the absorbent core is be formed from thin absorbent structures such as synthetic fibers, including spunbonded, melt blown card and bind staple fibers; and cellulosic fibers such as wood pulp, stablized wood pulp, wood pulp with superabsorbent, peat moss board, tissue paper, creped wadding; and the like. "Thin" absorbent structures preferably have a thickness of less than about 5 mm, preferably about 3 mm. Thus, a pleated absorbent core having three layers of absorbent structure would preferably have an overall thickness of less than about 1.5 cm, and more preferably about 1 cm. In order to ensure the integrity of the product during articulation between the folded, substantially planar configuration and the expanded three-dimensional structure, the absorbent structure preferably has a tensile strength of at least about 0.01 lbs/inch width. More preferably, the tensile strength is at least about 0.05 lbs/inch width.

Preferably, the absorbent core has a capacity of at least about 20 mL of urine. More preferably, the capacity is about 20 to 100 mL, and most preferably, about 20 to 50 mL. To increase the capacity, superabsorbent materials may be included in the absorbent core 24. Superabsorbent materials can include, without limitation, polyacrylates; modified natural and regenerated polymers such as polysaccharides; hydrocolloids; cross-linked nonionic polymers; derivatives of isobutylene-maleic anhydride copolymers; and the like. The superabsorbent material may be powdered or in fiber form. Preferably, the superabsorbent material is a powdered or fibrous polyacrylate superabsorbent.

The components and the composite structure of the absorbent product may be disposable or they may be durable, i.e., capable of withstanding laundering for several uses. Both disposable and durable products are well known in the industry. The skilled artisan will recognize that most of the components listed above are useful in both disposable and durable products.

The incontinence product can be produced by forming a continuous web of a composite absorbent material having a first layer which is a cover sheet 12, a second layer which is an absorbent core 24 and a third layer which is a barrier material 14. This composite web preferably has a length dimension substantially greater than a width dimension, such as a continuous web useful in an automated manufacturing process. This material can then be cut, e.g., by die cutting, to form a blank 26 as shown in FIG. 5. The blank 26 can then be pleated along fold lines 20 to result in the incontinence product 10 shown in FIGS. 1–3. The periphery 16 can then be treated prevent the pleats 22 from substantial expansion during manipulation of the product 10. This treatment may fully secure the pleats or it may include the use of expandable means such as elastic. Of course, the material can be pleated before the blank is cut, and indeed, a supply of material can be pleated before a series of products are stamped or cut from the material. These pleats can be in the form of at least one longitudinal pleat which forms the pleat(s) in several cut out products, or they can be in the form of a series of transverse pleats, at least one of which is located in each product.

Figure 6A:
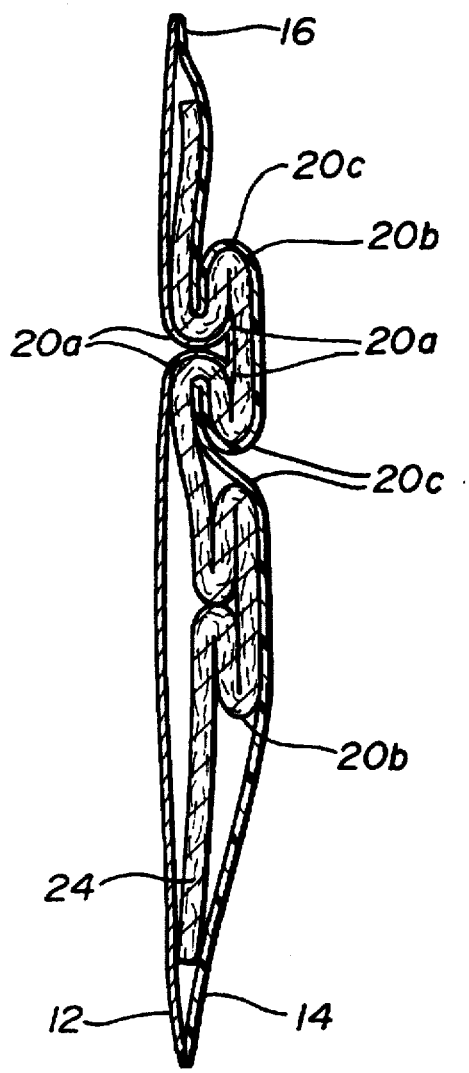
FIGS. 6a and 6b are sectional views, similar to FIG. 3, of alternative embodiments of the incontinence product of FIGS. 1–3.
Figure 6B:
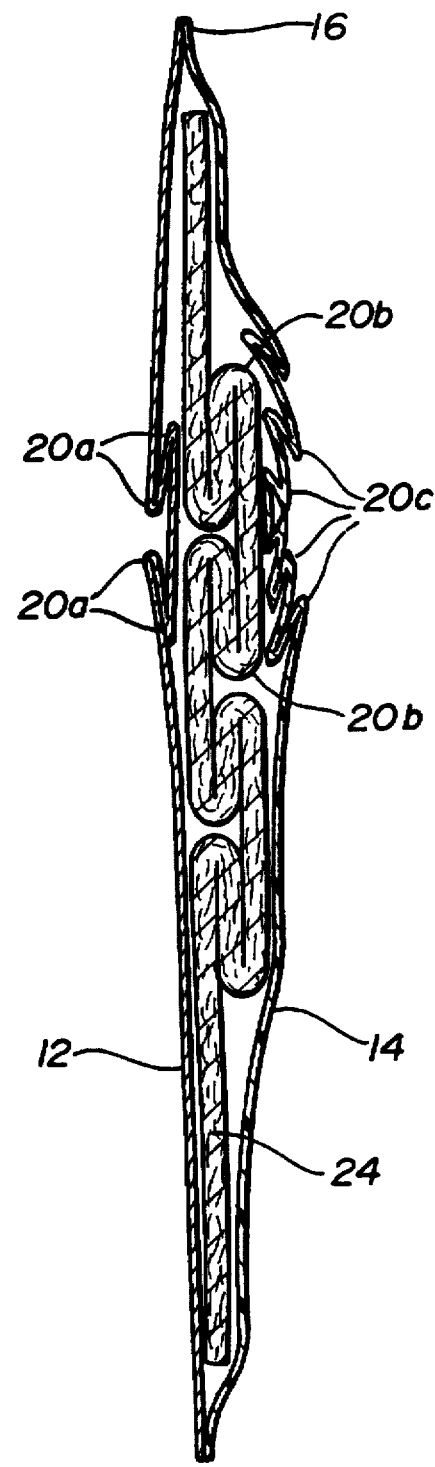

An alternate method of making this product would be to independently cut and pleat the cover sheet 12, absorbent core 24 and barrier material 14. Such independent production of these materials allows for variations in the product, such as illustrated in FIGS. 6a and 6b. In this embodiment, the cover sheet 12 has only four folds 20a, while the absorbent core has eight folds 20b, and the barrier has as many as twelve folds 20c. The increasing number of folds 20 in each material allows for different amounts of material to be used in each side of the product. Thus, the concave body-facing side 12 of the product need not use as much material as the convex garment-facing side 14. In addition, this embodiment illustrates the use of an absorbent core 24 which is not secured in the seal between the cover sheet 12 and barrier material 14 at the periphery 16 of the product. Again, the various layers which make up the product can be pleated before being combined to form a layered material supply. The products can then be cut or stamped out of this layered, folded supply.

While the discussion above generally relates to absorbent products having at least one pleat which traverses the absorbent product and is secured at both ends at the periphery, absorbent products having only one end of the pleat secured to prevent expansion at a first edge of the product and being unsecured to permit expansion across the interior of the product and at the second edge of the product are also contemplated. This effect is similar to that achieved by the embodiment of FIGS. 10–12, described below.

Figure 7:
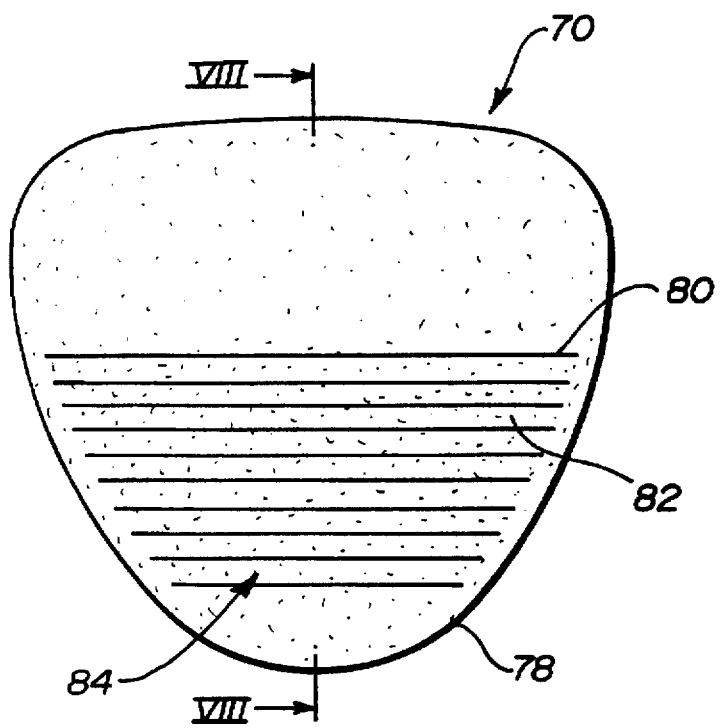
FIG. 7 is a plan view of the body-facing side of an alternative embodiment of an incontinence product in a substantially planar configuration.
Figure 8:
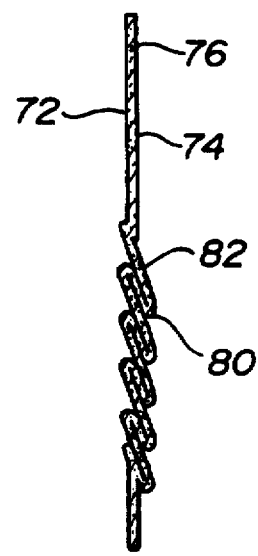
FIG. 8 is a sectional view along line VIII—VIII of FIG. 7.
Figure 9:
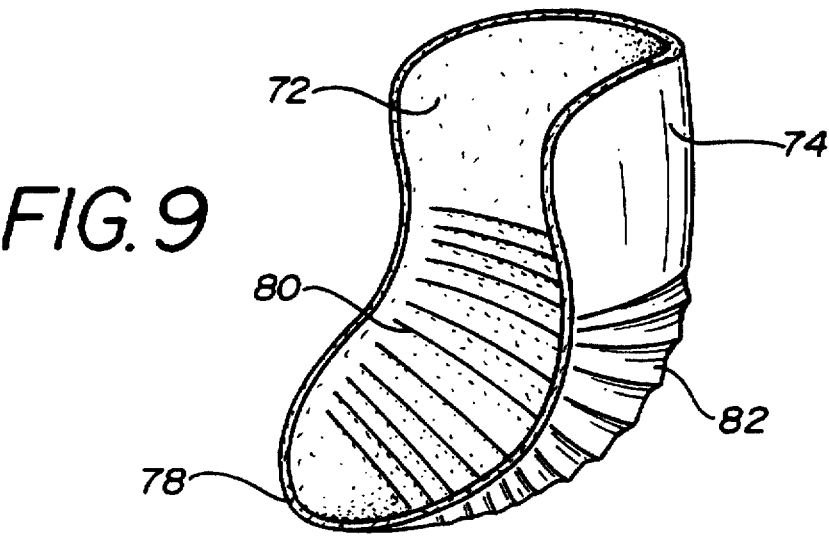
FIG. 9 is a perspective view of the incontinence product of FIGS. 7–8 in an expanded configuration.

Another alternative embodiment of the invention is disclosed in FIGS. 7–9. While this embodiment is similar to that of FIGS. 1–4, there are substantially more folds and pleats. In particular, the incontinence product 70 again has a body-facing side 72 and a garment facing side 74 which enclose an absorbent core 76. Again, the periphery 78 is secured, and there are a plurality of folds 80 forming pleats 82 in the interior 84 of the product. Thus, the product can be manipulated between a substantially two-dimensional structure as shown in FIGS. 7 and 8 to the three-dimensional structure illustrated in FIG. 9.

Figure 10:
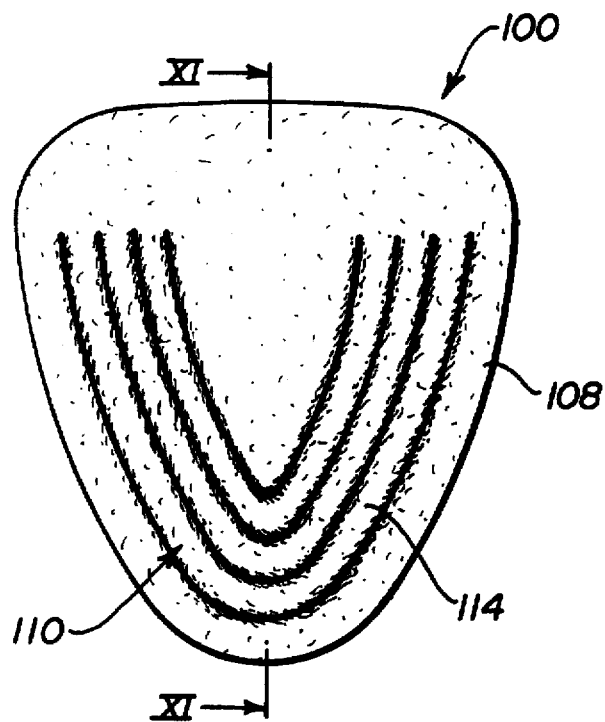
FIG. 10 is a plan view of the body-facing side of an alternative embodiment of an incontinence product in a substantially planar configuration.
Figure 11:
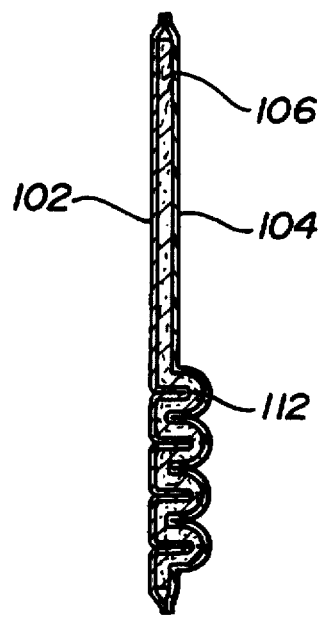
FIG. 11 is a sectional view along line XI—XI of FIG. 10.
Figure 12:
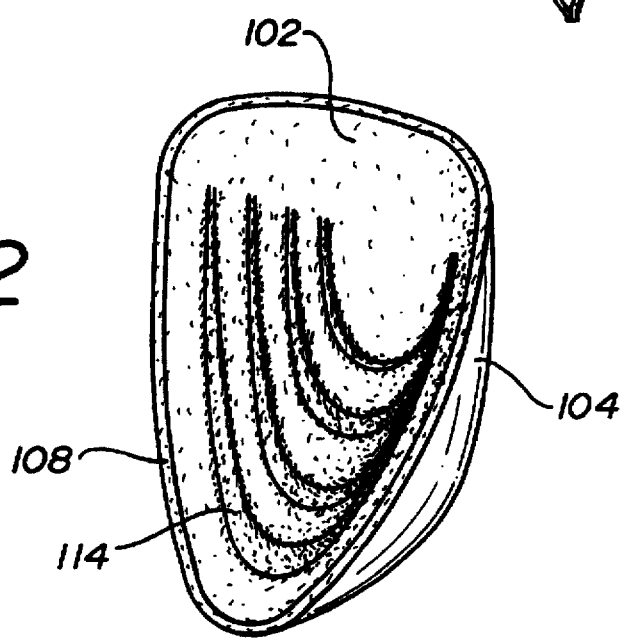
FIG. 12 is a perspective view of the incontinence product of FIGS. 10–11 in an expanded configuration.

Yet another alternative embodiment is disclosed in FIGS. 10–12. Again, the product 100 has a body-facing side 102, a garment facing side 104 and an absorbent core 106. The periphery 108 of the product 100 is secured, and the interior 110 has a plurality of folds 112 forming pleats 114. The folds 112 are arranged substantially parallel to one another, and they are U-shaped, following the contour of the left and right sides of the generally triangular incontinence product 100. The folds 112 and pleats 114 are arranged to produce an essentially planar body-facing surface 102 when the product is collapsed into an essentially two-dimensional configuration for storage.

Figure 13:
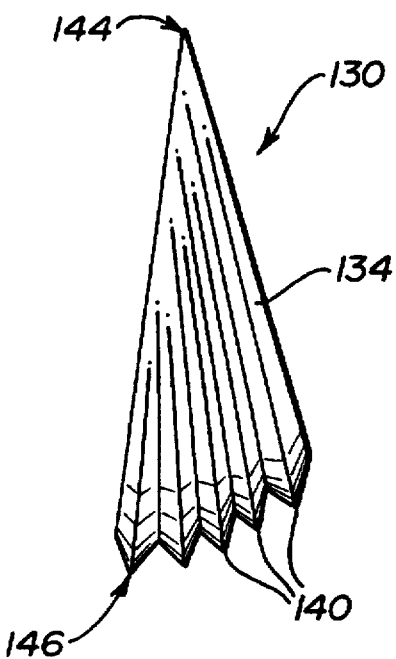
FIG. 13 is a side view of an alternative embodiment of an incontinence product in an expanded configuration.
Figure 14:
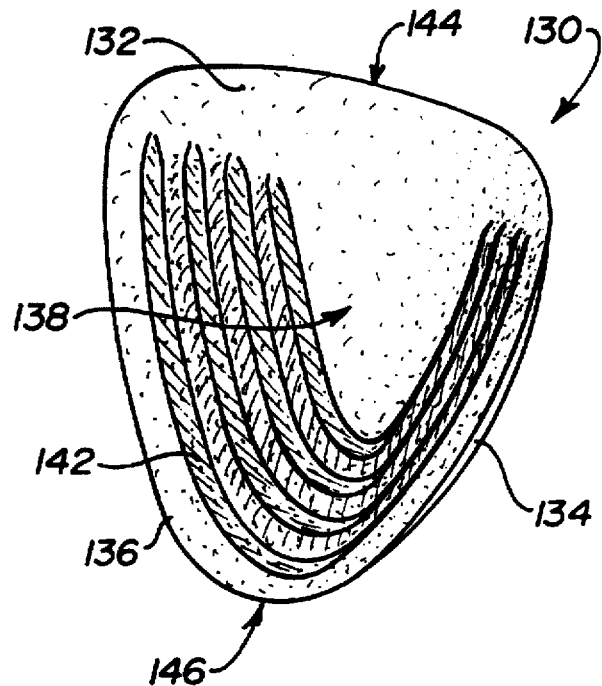
FIG. 14 is a perspective view of the incontinence product of FIG. 13 in an expanded configuration.

A further alternative embodiment is illustrated in FIGS. 13 and 14. The product 130 has a body-facing side 132, a garment facing side 134 and an absorbent core (not shown). The periphery 136 of the product 130 is secured, and the interior 138 has a plurality of folds 140 forming pleats 142. The folds 140 are arranged substantially parallel to one another, and they are U-shaped, following the contour of the left and right sides of the generally triangular incontinence product 130. However, in this embodiment, the folds 140 and pleats 142 are arranged accordion-like. Thus, when the incontinence product 130 is collapsed for storage before use, the essentially two-dimensional has an increasing thickness from the top 144 to the bottom 146 of the product 130.

Figure 15:
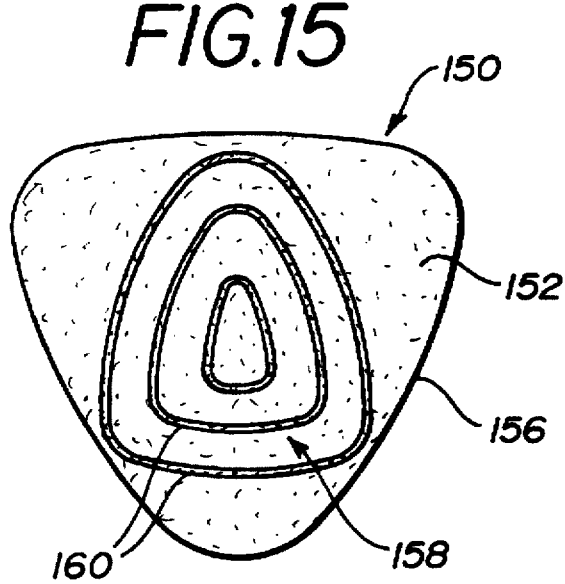
FIG. 15 is a plan view of the body-facing side of an alternative embodiment of an incontinence product in a substantially planar configuration.
Figure 16:
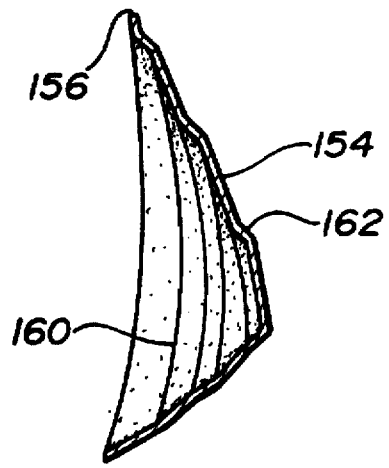
FIG. 16 is a side view of the incontinence product of FIG. 15 in an expanded configuration.

Another embodiment is illustrated in FIGS. 15 and 16. The product 150 has a body-facing side 152, a garment facing side 154 and an absorbent core (not shown). The periphery 156 of the product 150 is secured, and the interior 158 has a plurality of folds 160 forming pleats 162. The folds 160 are arranged substantially parallel to one another in a concentric manner. The folds 160 are arranged to expand into a substantially pyramidal shape to comfortably hold the male genitalia. In particular, the folds 160 are substantially triangular in shape. Again, the incontinence product 150 may be collapsed for storage before use in an essentially substantially planar configuration.

Figure 17:
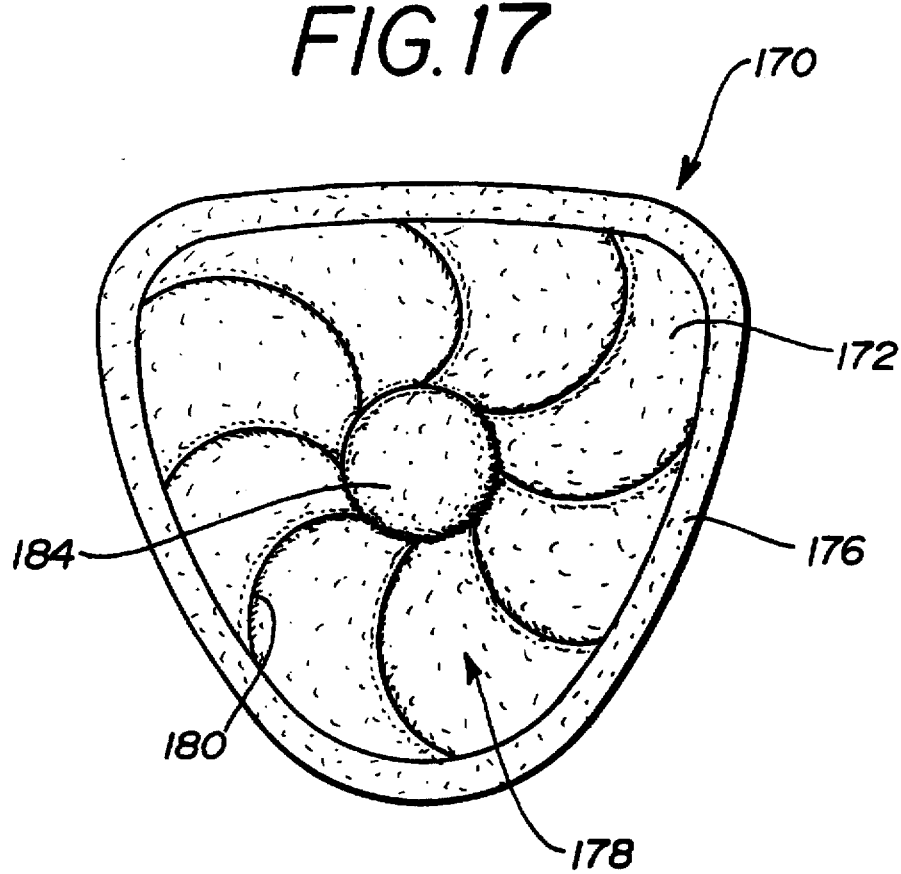
FIG. 17 is a plan view of the body-facing side of an alternative embodiment of an incontinence product in a substantially planar configuration.
Figure 18:
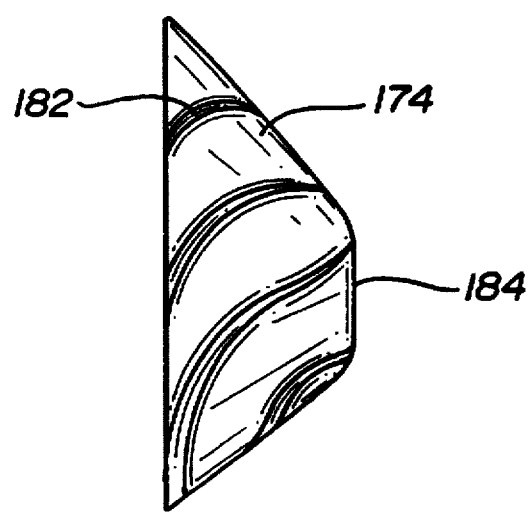
FIG. 18 is a side view of the incontinence product of FIG. 17 in an expanded configuration.

A final embodiment is disclosed in FIGS. 17 and 18. The product 170 has a body-facing side 172, a garment-facing side 174 and an absorbent core (not shown). The periphery 176 is secured, and the interior 178 has a plurality of folds 180 forming pleats 182. The folds 180 are arranged and configured to radiate in a curvilinear manner from an approximately centrally-located disc 184. Thus, the product 170 can be manipulated from an essentially flat, substantially planar configuration before use to a three-dimensional, cup-like receptacle for use by spiralling out the central disc 184.

The specification and drawings discussed above are presented to aid in the complete and non-limiting understanding of the invention disclosed herein. Since many variations and embodiments of the invention can be made without departing from its spirit and scope, the invention resides in the claims hereinafter appended.

What is claimed is:

1. An absorbent product useful as a male incontinence device comprising: a fluid-permeable, body-facing surface; a liquid-impermeable surface; and a thin absorbent structure therebetween having a tensile strength of at least about 0.01 lbs/inch width; wherein (1) the product has a periphery and an interior, (2) the body-facing surface and the liquid-impermeable surface substantially enclose the absorbent structure, (3) the product has at least one pleat to allow the interior to be expanded from a folded configuration to an expanded configuration, (4) the periphery of the product is arranged and configured to resist substantial perimetric expansion wherein the product is capable of being articulated between a substantially planar structure and a three-dimensional, cup-like structure for use.

2. The product of claim 1 having a plurality of pleats.

3. The product of claim 2 wherein the pleats are substantially parallel.

4. The product of claim 2 wherein the pleats are substantially concentric.

5. The product of claim 2 wherein the pleats are substantially equally spaced.

6. The product of claim 2 wherein the pleats extend radially from a central portion of the interior toward the periphery.

7. The product of claim 1 wherein the at least one pleat extends across the interior to the periphery and is restricted to resist substantial unfolding of the at least one pleat at the periphery.

8. The product of claim 1 wherein the product has a maximum length dimension which is not less than a maximum width dimension.

9. The product of claim 8 wherein the product is substantially symmetrical about a longitudinal axis, and the longitudinal axis corresponds to the length dimension.

10. The product of claim 9 wherein the at least one pleat is substantially perpendicular to the longitudinal axis.

11. The product of claim 9 wherein the at least one pleat is substantially parallel to the longitudinal axis.

12. The product of claim 8 which has a generally triangular shape to correspond to a male human's pubis.

13. The product of claim 1 wherein the absorbent structure comprises a superabsorbent material.

14. The product of claim 1 wherein the periphery is adhesively sealed.

15. The product of claim 7 wherein the periphery comprises elastic means.

16. The product of claim 1 wherein the at least one pleat extends from a first edge of the product, across the interior of the product and to a second edge of the product.

17. The product of claim 16 wherein the at least one pleat is secured to prevent expansion at the first edge of the product and is unsecured to permit expansion across the interior of the product and at the second edge of the product.

18. The product of claim 1 wherein the thin absorbent structure has at least one pleat.

19. The product of claim 1 which has an absorbent capacity of less than about 100 mL of urine.

20. The product of claim 1 wherein the thin absorbent structure essentially completely fills the product when articulated into the three-dimensional structure.

21. An absorbent product useful as a male incontinence device comprising: a liquid-permeable, body-facing surface; a liquid-impermeable surface; and a thin, pleated absorbent structure therebetween having a tensile strength of at least about 0.01 lbs/inch width and an absorbent capacity of less than about 100 mL of urine; wherein (1) the product has an essentially triangular periphery and an interior, (2) the body-facing surface and the liquid-impermeable surface substantially enclose the absorbent structure, (3) the product has at least one pleat located in the interior of the product to allow the interior to be expanded from a folded configuration to an expanded configuration, (4) the periphery of the product is arranged and configured to resist substantial perimetric expansion whereby the product is capable of being articulated between a substantially planar structure and a three-dimensional, cup-like structure for use, and (5) the thin absorbent structure essentially completely fills the product when articulated into the three-dimensional structure.

* * * * *